United States Patent [19]

Rise et al.

[11] Patent Number: 5,752,930
[45] Date of Patent: May 19, 1998

[54] IMPLANTABLE TECHNIQUES FOR INFUSING EQUAL VOLUMES OF AGENTS TO SPACED SITES

[75] Inventors: Mark T. Rise, Monticello; Michael D. Baudino, Coon Rapids, both of Minn.

[73] Assignee: Medtronic, Inc., Minneapolis, Minn.

[21] Appl. No.: 717,047

[22] Filed: Sep. 20, 1996

Related U.S. Application Data

[63] Continuation-in-part of Ser. No. 431,183, Apr. 28, 1995, abandoned.

[51] Int. Cl.⁶ .................................................. A61M 31/00
[52] U.S. Cl. .......................... 604/53; 604/49; 604/891.1; 604/48; 604/93; 604/257
[58] Field of Search .............................. 604/93, 890.1, 604/891.1, 19.48, 257, 259, 200, 131, 153, 154, 155, 152, 151, 53, 49

[56] References Cited

U.S. PATENT DOCUMENTS

| | | | |
|---|---|---|---|
| 4,193,397 | 3/1980 | Tucker et al. | 604/93 X |
| 4,871,351 | 10/1989 | Feingold | 604/93 X |
| 4,978,338 | 12/1990 | Melsky et al. | 604/93 |
| 5,085,644 | 2/1992 | Watson et al. | 604/93 X |
| 5,395,324 | 3/1995 | Hinrichs et al. | 604/93 X |

*Primary Examiner*—Michael Powell Buiz
*Assistant Examiner*—N. Kent Gring
*Attorney, Agent, or Firm*—Curtis D. Kinghorn; Harold R. Patton

[57] ABSTRACT

An implantable catheter defining a plurality of fluid exits responsive to a first range of pressure on a fluid agent for delivering substantially the same flow rate of the agent through each of the exits into spaced infusion sites and responsive to a second range of pressure less than a threshold pressure on the agent for inhibiting the flow of the agent from any of the exits into any of the sites. A first pressure in the first range is applied to the agent in the catheter for a first time period and a second pressure in the second range is applied for a second time period to the agent in the catheter so that substantially the same dosage of agent can be applied to each of the sites.

23 Claims, 7 Drawing Sheets

IMPLANTABLE TECHNIQUES FOR INFUSING EQUAL VOLUMES OF AGENTS TO SPACED SITES

BACKGROUND OF THE INVENTION

This is a continuation-in-part of application Ser. No. 08/431,183 filed on Apr. 28, 1995, now abandoned.

FIELD OF THE INVENTION

This invention relates to an implantable system for infusing a therapeutic agent into an organism and more particularly relates to such a system for delivering equal volumes of a therapeutic agent into spaced infusion sites at low dosages.

DESCRIPTION OF THE RELATED ART

When chronic administration of a pharmaceutically active agent is required, internal delivery by an implantable infusion pump ("IIP"), in combination with a catheter, may be the desired delivery means. For example, IIP-catheter delivery may be preferred when the site specific delivery of the agent is critical, or the agent must be administered to spaced sites in tightly controlled, yet minute dosages.

In current catheter designs, the agent is ordinarily delivered to the spaced sites via a fixed number of elution holes. The fixed number of elution holes makes it difficult to tailor the catheter to the flow rates dictated for a particular agent and a particular parenchymal target. In many neurological applications, the quantity of delivered agent is relatively minute and must be carefully tailored. For low agent dosages, experience has shown that the flow rate of the agent is not uniform through all elution holes. In particular, at low flow rates, fluid moving down the catheter exits the catheter at the elution hole having the least fluid resistance to flow so that relatively little or no fluid exits the catheter through the remaining elution holes. This results in overdosage to some sites (the elution hole with the least fluid flow resistance) and underdosage to other sites (the remaining elution holes). The present invention is directed to solving this problem.

SUMMARY OF THE INVENTION

The invention is useful in a system for infusion of a predetermined dosage of liquid agent to a plurality of infusion sites located at spaced intervals in a portion of a body to be treated by the agent. According to a preferred practice of the invention, a catheter is implanted in the body. The catheter has a plurality of fluid exits for preferentially delivering substantially the same flow rate of the agent through each of the exits into the desired sites. When a pressure less than a threshold pressure is applied to the catheter, the flow of the agent from any of the exits into any of the sites is inhibited.

Pressure is applied to the agent in the catheter at a first pressure in the first range and at a second pressure in the second range. The first pressure is larger than the second pressure. The first pressure is sufficiently large so the fluid is moved under pressure along the catheter to contact all the elution openings and overcome the fluid resistance that prevents the flow of fluid out of the elution openings. Under this high pressure, and according to fluid dynamics, the fluid will be presented to all the elution openings at approximately the same pressure.

The infusion of a predetermined dosage to the infusion sites is controlled by applying the first high pressure for a predetermined first time period. The first time period will typically be relatively short. As a result of applying a high pressure for a short time, the dose, which is directly proportional to the product of the time of applying the first pressure and the first pressure, will be the desired dose. After the first pressure has been applied for the first time period, a second pressure is applied for a predetermined second time period. The second pressure is less than the first pressure and is preferably zero. The average flow rate is the dose divided by the sum of the time the first pressure is applied and the time the second pressure is applied.

As can be seen, by using the forgoing techniques, the dose of fluid delivered by the catheter will be the desired dose despite the fact that the flow rate during the first time period when the first high pressure is applied is much higher than the flow rate during the time that the second pressure is applied. As a result, the risk of underdosage or overdosage at any desired site is reduced.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 2:
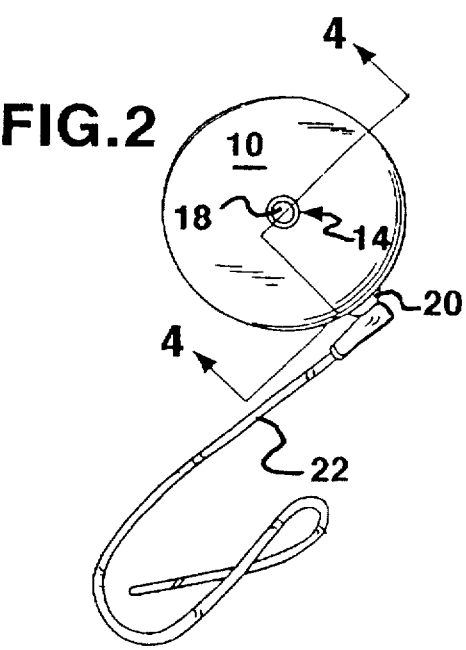
FIG. 2 is a plan view of the device shown in FIG. 1.
Figure 1:
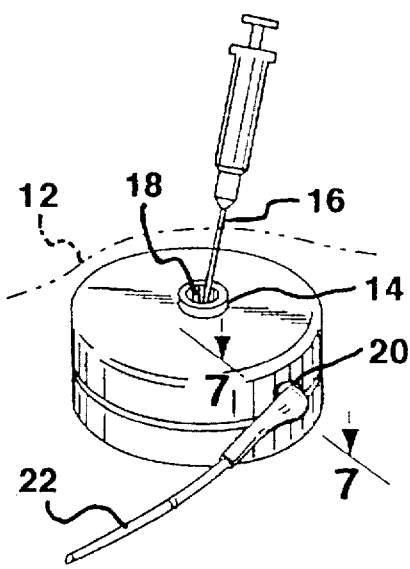
FIG. 1 is a diagrammatic view of a preferred form of device made in accordance with the present invention implanted beneath skin (shown in phantom) with a reservoir of the device being filled by a hypodermic syringe.

Referring to FIGS. 1 and 2, an administration system or device 10 made in accordance with the preferred embodiment is shown implanted below a layer of skin 12 indicated in phantom. The administration device has a port 14 into which a hypodermic needle 16 can be inserted through the skin 12 to insert a quantity of a liquid agent through a septum 18 into a drug reservoir 19 (FIG. 4) located within drug administration device 10. Examples of liquid agents include, but are not limited to, medications, growth factors, antisense agents, ionic solutions, antibodies, hormones, proteins or peptides, viruses, cell suspensions, chemotherapeutic agents or toxins, or drugs. The liquid agent is delivered from device 10 through a catheter port 20 to which a catheter 22 is attached. The catheter 22 has means positioned to deliver the agent to desired infusion sites.

Figure 3:
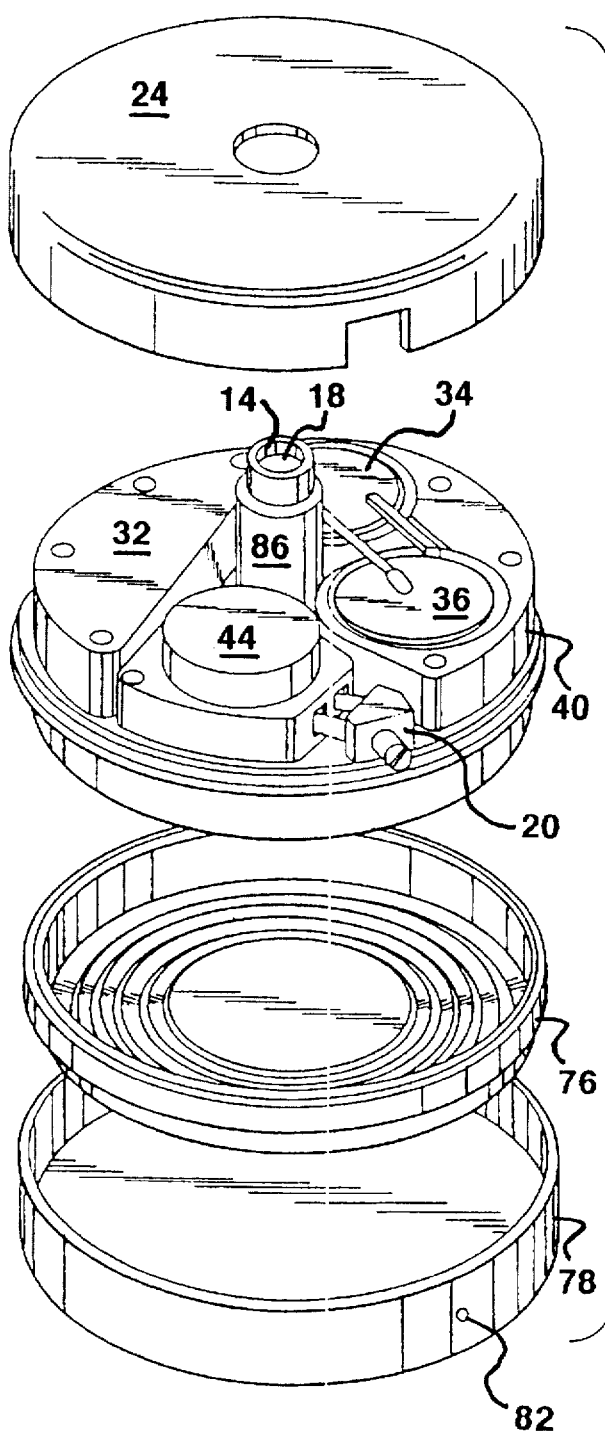
FIG. 3 is an exploded view of the device shown in FIG. 1 with the catheter removed.

Referring to FIG. 3, a circuit module 32 is driven by suitable batteries 34 and 36 which are connected to battery input terminals of an electronic module 32.

Figure 7:
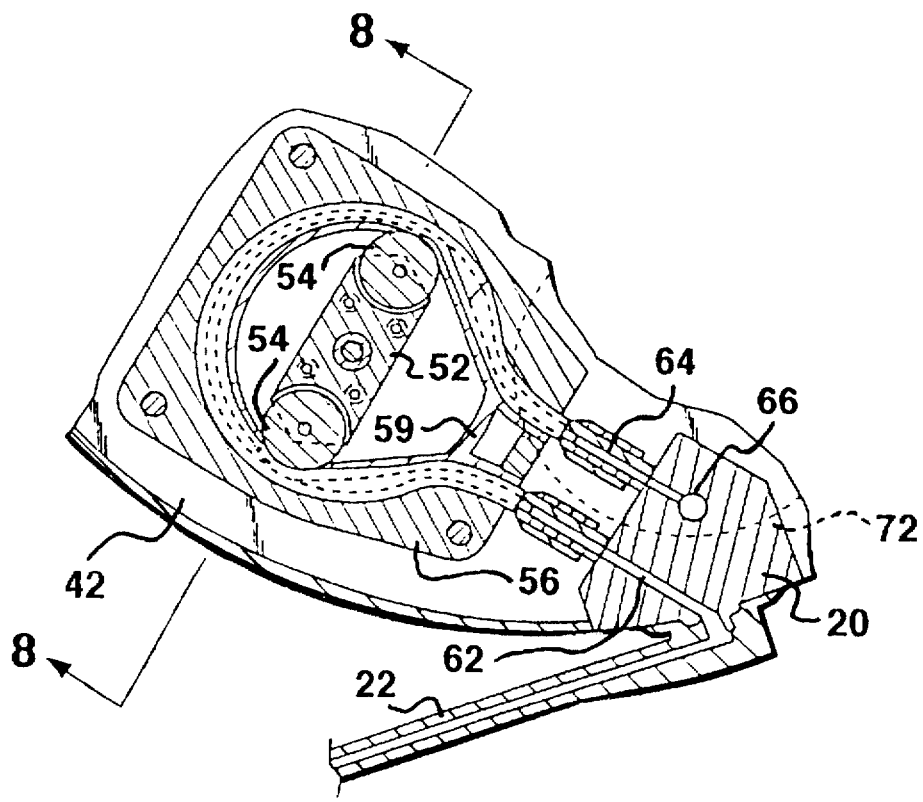
FIG. 7 is a cross sectional view of a pump/meter of the device taken along line 7—7 of FIG. 1.
Figure 8:
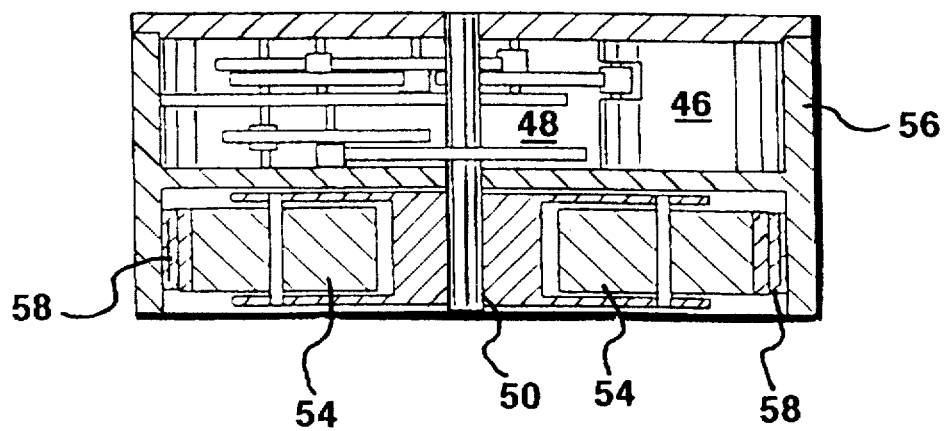
FIG. 8 is a cross sectional view of the pump taken along line 8—8 of FIG. 7.

A roller pump 44 is shown in more detail in FIGS. 7 and 8. A exemplary commercially available pump 44 is the Syncromed® Infusion Pump made and sold by Medtronic, Inc. in Minneapolis, Minn. A motor 46 drives a gear train 48, which in turn drives a shaft 50 that is connected to an arm 52. Motor 42 is a two pole subminiature stepping motor of the type used in digital watches having analog time indicating means. Such motors are manufactured by Seiko Corporation. The winding of motor 42 is driven by electrical pulses from electronics module 32 which step the motor through a fixed arc for each pulse.

Rollers 54 are each mounted for rotation about their axes at both ends of arm 52 which is rotatable through 360°. As shaft 50 is rotated, arm 52 and rollers 54 are rotated about the axis of shaft 50. The arm is located within a housing 56 and a flexible tube 58 lines the interior wall of housing 56 as shown in FIG. 7. A shim 59 is interposed between rollers 54 and tubing 58 to aid in balancing the forces applied to shaft 50 as rollers 54 traverse a complete revolution of shaft 50. As shaft 50 rotates, the wheels 54 roll along shim 59 and compress tubing 58 against the inner wall of housing 56.

Figure 5:
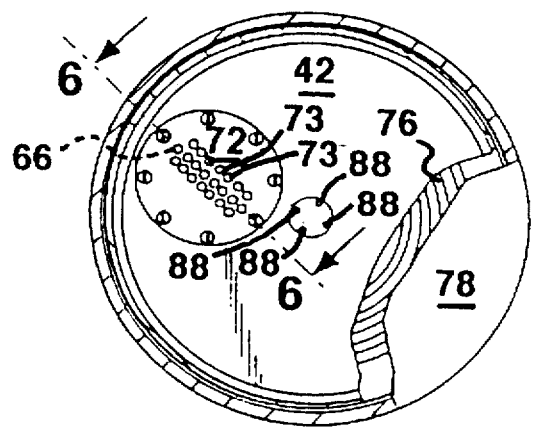
FIG. 5 is a cutaway bottom plan view of the device with portions cutaway to reveal the reservoir and associated elements.
Figure 6:
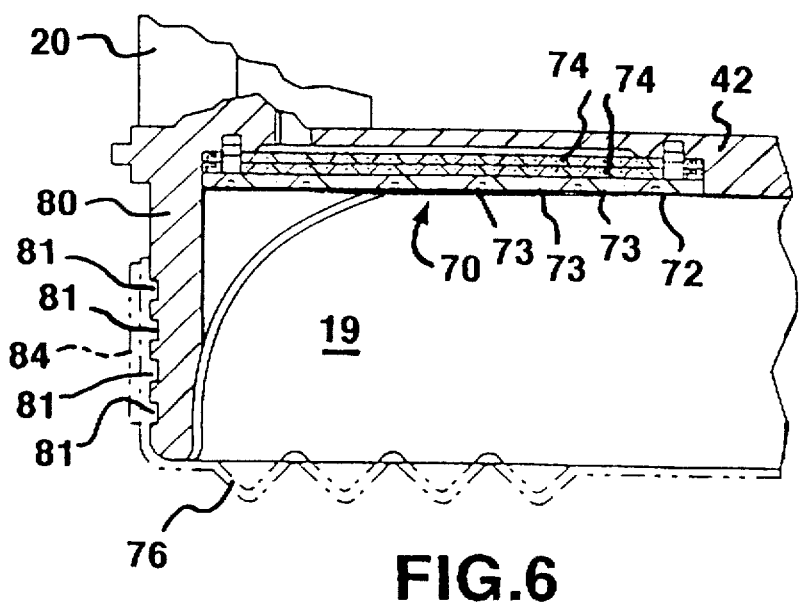
FIG. 6 is a cross sectional view of a filter of the device taken along line 6—6 of FIG. 5 and a detail of FIG. 4 taken at 8 and shown in enlarged scale.

Pump 44 is connected to catheter port 20 which provides an outlet conduit 62 that is connected to catheter 22 screwed onto port 20. Pump 44 receives its input from an inlet conduit 64 which is connected to an inlet port 66 that communicates with fluid reservoir 19 through a filter 70 shown in FIG. 5 and in cross section in FIGS. 4 and 6. As shown in FIG. 6, filter 70 comprises a clamping ring and screen 72 which has a number of holes 73 for permitting the flow of a liquid through the filter. The clamp ring and screen 72 holds a pair of fine filters 74 for screening out any particles of skin or hair which could have reached fluid reservoir 19 when the reservoir is filled utilizing a hypodermic needle inserted through the patient's skin.

Reservoir 19 is formed with its top portion being the underside of housing 42 and its lower portion formed from a flexible diaphragm 76 that is protected by a lower shield 78 which forms a seal against a projecting flange 80. The flange has a plurality of circumferential sealing grooves 81 which project from housing 42. Upper shield portion 24 also is seated against flange 80. The diaphragm is secured to housing 42 with a circumferential Teflon band 84 and a suitable adhesive to form a sealed reservoir.

After sealed reservoir 19 has been formed and lower shield 78 has been positioned against flange 80 of housing 42, the space between diaphragm 76 and lower housing 78 is evacuated through hole 82 shown in FIG. 3, and a small amount of a suitable fluorocarbon liquid is inserted in the hole to backfill the device. Hole 82 is then welded to seal the unit. In one embodiment, approximately 2.5 CCs of Fluorinert FIC88 is inserted in the unit. The amount of fluorocarbon fluid, or other suitable volatile fluid, is selected to provide a positive pressure against bellows 76 when the administration device is implanted in the patient's body. As is well known in the art, such a volatile fluid exerts a constant vapor pressure at a given temperature regardless of volume. Thus, the constant positive pressure compresses bellows 76 and urges the liquid contents of the reservoir 19 through filter 70. The fluid is forced through screen 72 and filter segments 74 to input port 66 of pump 44. As pump 44 rotates, the rolling action of rollers 54 at the ends of arm 52 allows a predetermined amount of liquid to be either pumped or metered from reservoir 19 through catheter 22 to the location within the body where it is desired to apply the fluid agent.

Figure 4:
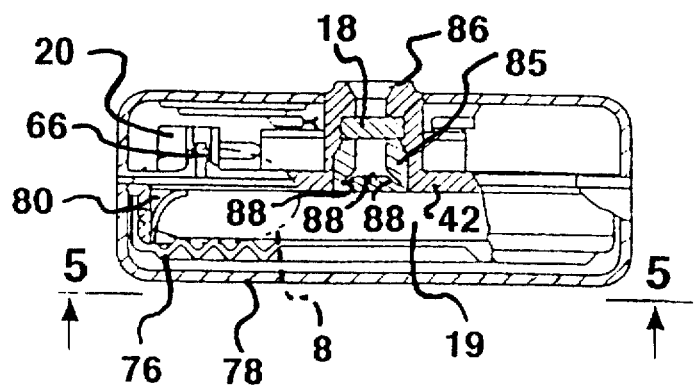
FIG. 4 is a cross sectional view of the device taken along line 4—4 of FIG. 2 to reveal the reservoir.

The fluid supply in the reservoir is periodically replenished by applying a hypodermic needle 16 as shown in FIG. 1. The hypodermic needle pierces the septum 18. As shown in FIG. 4, the septum 18 is seated against a plug 85. Plug 85 and septum 18 are mounted in a projecting neck portion 86 of housing 42. Neck portion 86 has a central opening to permit access to septum 18 by hypodermic needle 16. Needle 16 is forced through the septum 18 which may be formed of a silicone rubber compound. If the hypodermic needle 16 has a rounded blunt tip and a delivery port located on the shaft of the needle, the insertion of the needle through the septum 18 will not cause a permanent hole to form in septum 18. After the hypodermic needle has been forced through the septum, its contents are delivered into the chamber in plug 85 under pressure when the pressure of its contents exceeds the pressure of reservoir 19, which is typically greater than 3 psi. The fluid is forced into reservoir 19 through apertures 88 in plug 85, and bellows 76 is expanded to accept the fluid. The hypodermic needle is then withdrawn and the silicone rubber of septum 18 reseals.

Electronic module 32 can be identical to the like numbered module shown in U.S. Pat. No. 4,692,147 that is incorporated by reference. Programming command information may be applied as taught in the foregoing U.S. patent.

Figure 9:
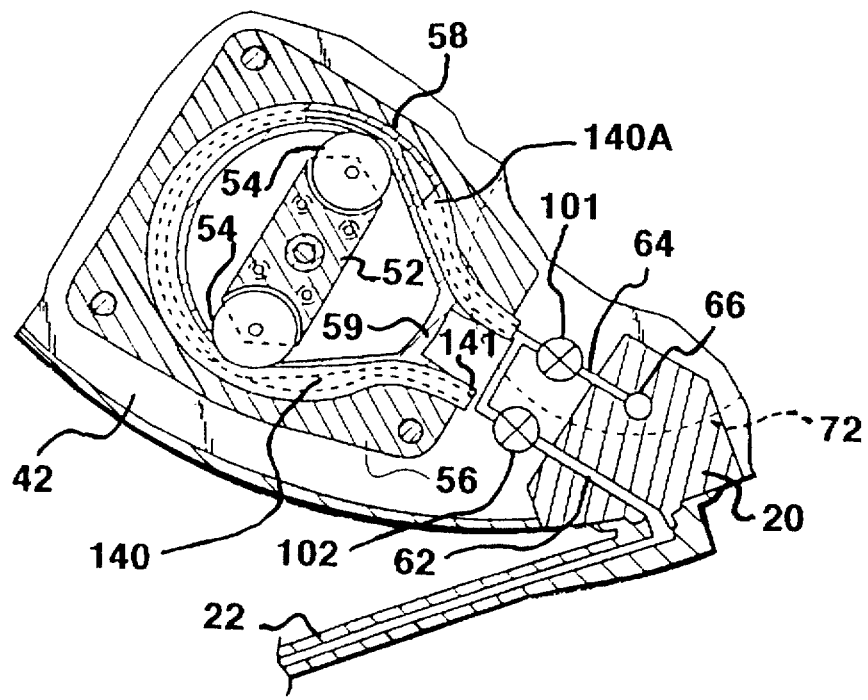
FIG. 9 is an alternative embodiment of the device shown in FIG. 7 with additional valves included.

Another embodiment of the device is shown in FIG. 9. In this embodiment, hollow passageway 140 of tube 58 is closed off at end 141 and electrically controlled valves 101 and 102 are inserted as shown. The valves are opened and closed by signals conducted from module 32 over conductors (not shown).

Figure 10:
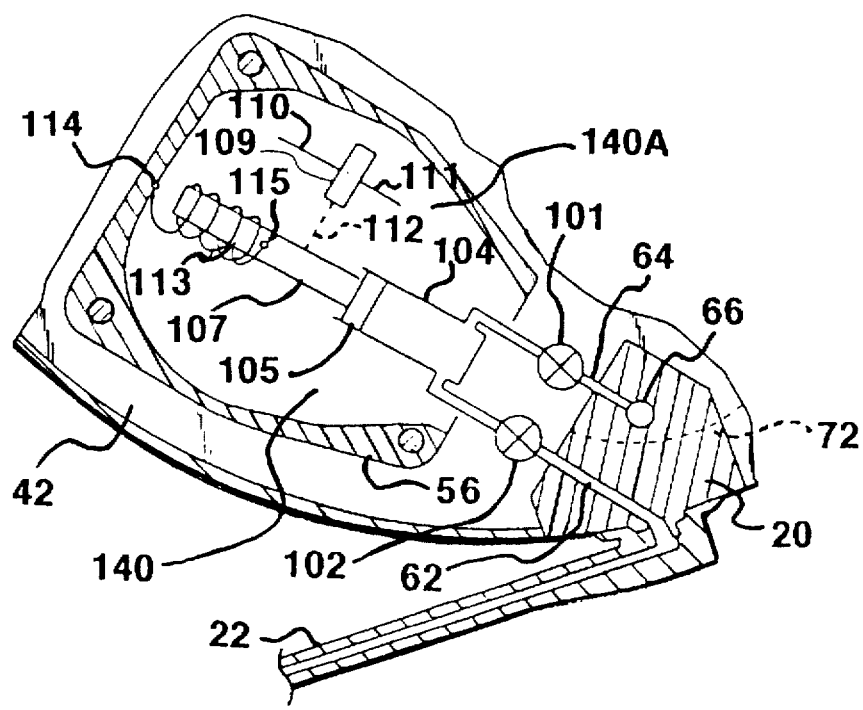
FIG. 10 is another embodiment of the device shown in FIG. 7 employing a cylinder, piston and solenoid.

FIG. 10 illustrates another embodiment of the invention employing a cylinder 104 which is fitted with a piston 105 capable of exerting pressure on the agent in catheter 22. The piston is moved by a connecting rod 107 which forms a portion of a conventional electrical solenoid including a solenoid coil 109 that is supplied with current through leads 110 and 111 that are connected to electronic module 32. The solenoid operates through a conventional solenoid linkage 112.

Connecting rod 107 is biased toward the left as shown in FIG. 10 by a conventional coil spring 113 that is connected to housing 56 at point 114 and is connected to rod 107 at point 115. When the solenoid is operated, it drives piston 105 to the right toward valves 101 and 102. If the supply of voltage to coil 109 is interrupted by control module 32, piston 105 is returned to the position shown in FIG. 10 by coil spring 113. For the embodiment shown in FIG. 10, no motor is required. As a result, the apparatus shown in FIG. 8 is unnecessary.

Figure 11:
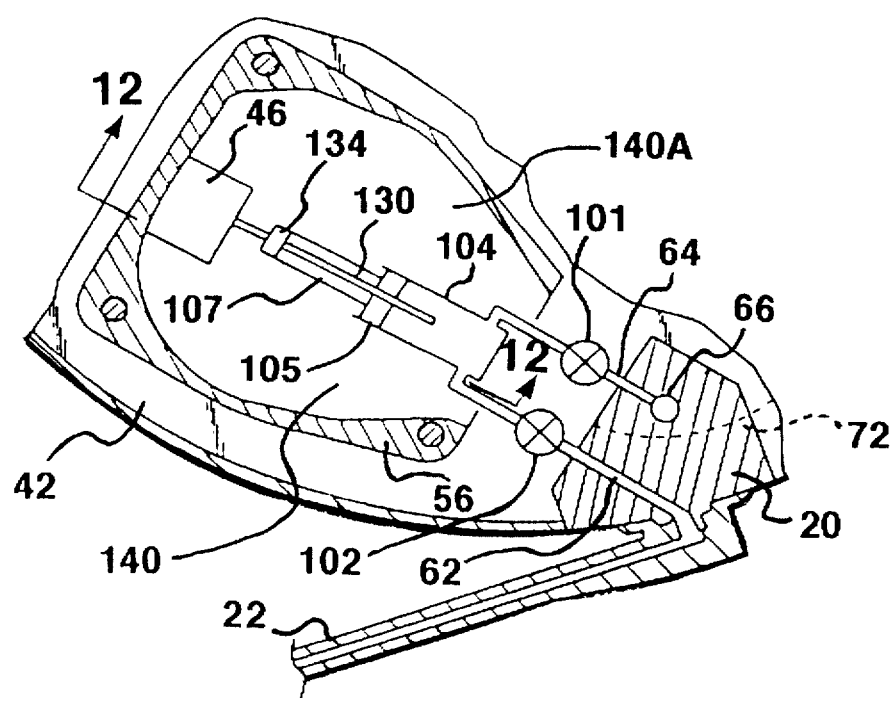
FIG. 11 is still another embodiment of the device shown in FIG. 7 employing a stepper motor and a worm gear drive.
Figure 12:
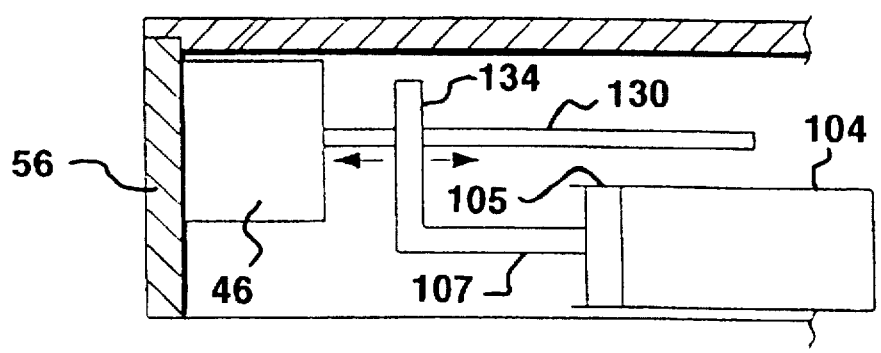
FIG. 12 is a fragmentary, sectional view taken along line 12—12 of FIG. 11.

Another embodiment of the device is shown in FIGS. 11 and 12. Motor 46 rotates a conventional worm gear 130. The threads in the gear engage comating threads in a drive arm 134 which is moved to the left or right as shown in FIG. 12 by rotation of gear 130 in opposed directions. Drive arm 134 is mechanically connected to connecting rod 107 which moves piston 105.

Figure 13:
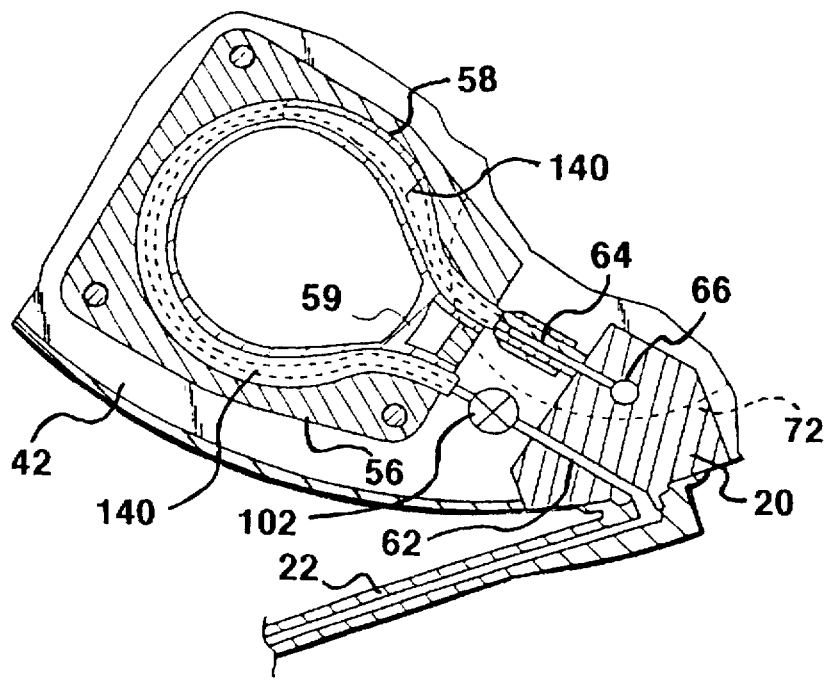
FIG. 13 is yet another embodiment of the device shown in FIG. 7.

Still another embodiment of the device is shown in FIG. 13. The pressure from bellows 76 (FIGS. 4 and 6) applies pressure to the liquid agent in passageway 140. The application of pressure to the agent in catheter 22 is controlled by valve 102 that opens or closes in response to electrical signals from module 32.

Figure 14:
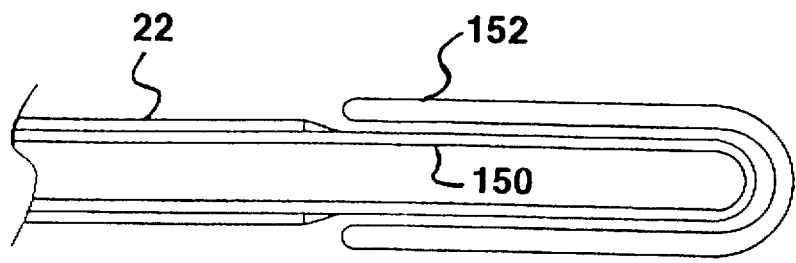
FIG. 14 is a fragmentary view of a preferred form of a catheter tip shown in section.

FIG. 14 illustrates one preferred form of a porous catheter tip 150 that is a press fit into the distal end of catheter 22 as shown. Tip 150 has a rounded cylindrical leading exterior surface to minimize disruption during insertion. In one application of the device, tip 150 projects into the brain although the tip 150 may be implanted in other organs or spaces in the body as well. Examples of these other organs or spaces in the body include, but are not limited to pancreas, liver, epidural or intrathecal spaces of the spinal canal, the heart, skeletal muscle and bowel.

Tip 150 is surgically implanted in the brain using well known stereotactic placement techniques, and catheter 22 is subsequently tunneled subcutaneously through the body to the location in the body where device 10 is implanted. Device 10 ordinarily is surgically implanted subcutaneously in the pectoral or abdominal region of the body. The size of catheter 22 and tip 150 are exaggerated in the drawings for ease of illustration of the structure.

Tip 150 has a generally tubular shape and is designed to fit snugly within the lumen of catheter 22. Catheter 22 and the external diameter of tip 150 should be sized so that there is zero tolerance between them. A snug fit is desirable to maintain the position of catheter tip 150 in relation to the catheter 22 and to discourage seepage of agent between the interface of the exterior of tip 150 and the interior surface of catheter 22.

Tip 150 preferably is composed of polysulfone hollow fiber, manufactured by Amicon, although a polyethylene, polyamides and polypropylene also are suitable. Tip 150 preferably is porous along its entire length to enable agent to flow into spaced sites 152. The preferred size of the pores in tip 150 is approximately less than or equal to 0.22 microns. A pore size of 0.22 micron is the standard bioretentive filter porosity. The problem of unequal distribution of agent through the pores of tip 150 become more manifest as the pore size increases to macroscopic levels. As a result, it is believed that the present invention will have greatest utility for tip 150 as the pore size approaches macroscopic size.

Tip 150 dispenses agent in a nearly 360° pattern along the entire length of tip 150 that is exposed to the parenchymal target presented in FIG. 14 by sites 152. Additional details of the tip may be obtained from pending U.S. application Ser. No. 08/439,960 entitled "Intraparenchymal Infusion Catheter System," filed on Apr. 28, 1995 in the name of Dennis Elsberry and assigned to the same assignee as the present application.

Figure 15:
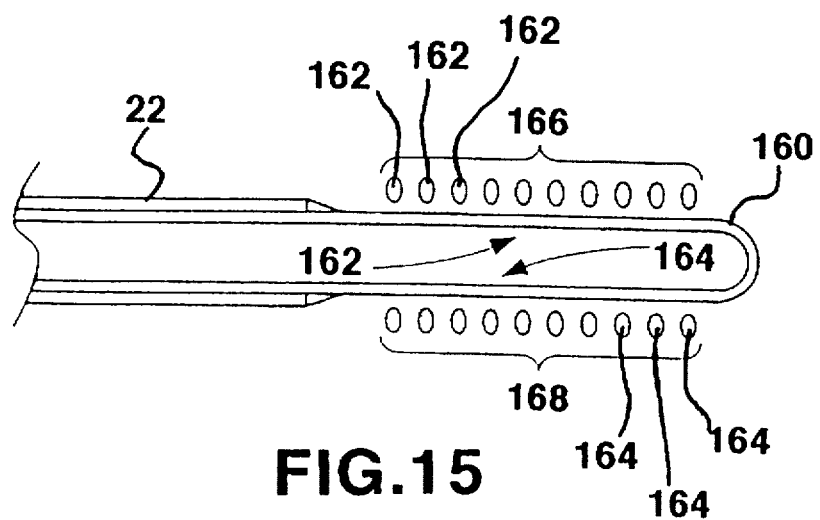
FIG. 15 is an alternative embodiment of a catheter tip shown in section.

FIG. 15 illustrates an alternative catheter tip 160 defining a plurality of infusion ports 162, 164. In one embodiment, catheter tip 160 has a first group of ten collinear cylindrical, discrete holes or ports 162 spaced equally apart and a second group of ten collinear cylindrical, discrete holes or ports 164 spaced equally apart. The holes in groups 162 and 164 are arranged in coaxial opposed pairs. The holes in group 162 supply agent to ten corresponding spaced infusions sites 166, and the holes in group 164 provide agent to ten corresponding spaced infusion sites 168. The infusion sites may be located in any portion of the body. In this embodiment, the number of holes must be at least two but may be more than the ten shown and described in this embodiment.

Figure 16:
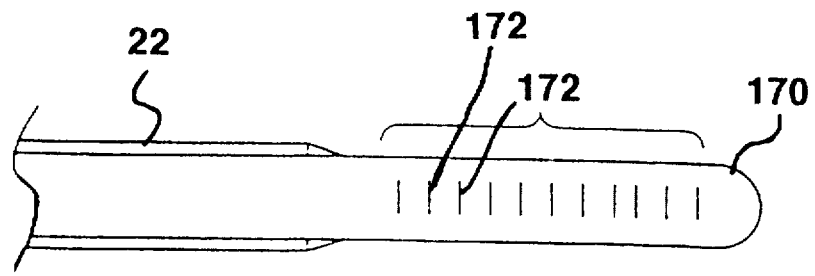
FIG. 16 is a top plan view of another embodiment of a catheter tip.

FIG. 16 illustrates another form of catheter tip 170 defining a plurality of slits 172. In one embodiment, catheter tip 170 has a group of ten slits 172 spaced equally apart. These slits 172 are cut through the thickness of tip 170 and preferably have a length of 0.25 to 2.0 millimeters, which is a common length for slits in prior art catheters. Alternatively, slits 172 may be rotated at any angle from the orientation shown in FIG. 16 and may be arranged at any spaced interval, whether regular or irregular, along the length of tip 170 and around the circumference of tip 170. In one such alternate embodiment, slits 172 may be rotates at a 90° angle from the orientation shown in FIG. 16. In this embodiment, the number of slits must be at least two but may be more than the ten shown and described in this embodiment.

It is difficult to make and use the catheter openings shown in FIGS. 14–16 in such a way that the openings all have the same resistance to fluid flow. The pressure required to cause a specific rate of fluid flow through the openings in the catheter tips varies depending on the viscosity of both the agent to be delivered and the surrounding medium into which the agent is being infused, as well as the dimensions of the openings. The more viscous the medium, the higher the pressure required to achieve flow from all of the openings in the catheter tip.

The applicants have discovered that agent can be infused substantially equally into spaced infusion sites by applying a first range of relatively high pressure on the agent in the catheter that will deliver substantially the same flow rate of the agent through each of the openings into the spaced sites. This relatively high pressure is usually, although not necessarily, considerably higher than the pressure applied in presently known agent delivery infusion systems. After equal fluid flow is achieved by application of a first relatively high pressure in the first range, the pressure on the agent and the catheter is substantially reduced to a second pressure in a second range that is less than a threshold pressure. The threshold pressure is the pressure below which the flow of the agent does not flow from any of the openings in the catheter tip into the infusion sites. By regulating the time period during which the first and second pressures are applied, the average flow rate can be adjusted to provide the proper dosage of the infusion agent.

Average desired flow rates for therapeutic infusion into the brain parenchyma, cerebral ventricles or intrathecal space is generally in the range of 0.01 microliter per hour to 20 microliters per minute, depending on the agent concentration and therapeutic application. The application of the first and second pressures for the prescribed time periods is illustrated by the timing diagram of FIG. 17 which shows the pressure exerted on the agent in catheter 22 and any of tips 150, 160 or 170.

Initially, the pressure in the catheter is at level P2 which is insufficient to produce any fluid flow through any of the openings in the catheter tip. For many applications, pressure P2 can be zero. During time period T1, a pressure wave 180 at pressure P1 is applied to the agent in catheter 22 and the catheter tip which is sufficient to deliver substantially the same flow rate from each of the openings in the catheter tip. During time period T1, when pressure P1 is applied to the agent in the catheter tip, approximately the same flow rate is exhibited through each of the openings in the catheter tip.

During portion 190 of the pressure wave, for time period T2, the pressure is reduced again to pressure P2. During the time period T2, there is no fluid flow through the openings of the catheter tip. Time period T2 is adjustable from 10 seconds to 672 hours.

After the proper dosage has been administered at the end of time period T2, the cycle of agent is begun again by applying pressure wave 200 to achieve pressure P1 for time period T1. The average flow rate is the flow achieved during T1 divided by the time that is the sum of T1 and T2.

In normal operation, the Syncromed® Infusion Pump produces the following flow rates in for the following uses:

for intrathecal infusion: about 200–1000 µliters/day (0.1389–0.6039 µliter/min.).

for intracranial infusion: about 100–500 µliters/day (0.0695–0.3020 µliter/min.).

for intravenous chemotherapy infusion: about 1000–2500 µliters/day (0.6039–1.510 µliter/min.).

Typical infusion pressures in the Syncromed® Infusion Pump are about 3–5 mm Hg for intrathecal infusion and about 5–10 mm Hg for intracranial infusion.

Our tests have shown that in a catheter having two infusion slits each 0.050" long, at a pressure of 30 mm Hg, 90% of the flow of the infusing agents exits the catheter through the first infusion slit. These tests have shown that this pattern of infusion is virtually independent of the separation distance of the slits. At this configuration and pressure, the flow rate is about 100 µliters/minute.

If the pressure is raised to 50 mm Hg, our tests show that the flow of the agent is roughly divided equally through both slits. With this configuration and at this higher pressure, the flow rate is about 200 µliters/minute. At this pressure, to achieve an average flow rate of 200 µliters/day (0.1389 µliters/min.), the ratio of time period T1 to time period T2 must be about $6.95 \times 10^{-4}$. A practical range for T1 is from 0.01 second to 2.0 seconds in duration. For T1 equal to 0.01 second, T2 should be about 14.39 seconds.

With a catheter having four slits each 0.050" long, our test show that at a pressure of 22 mm Hg, virtually all the agent exited the catheter through the first slit. With this configuration and pressure, the flow rate is about 100 µliters/minute. Increasing the pressure to 35 mm Hg results in agent flow out of three of the four slits with a flow rate of about 250 µliters/minute.

When the pressure is increased to 50 mm Hg, agent flows virtually uniformly out of all four slits at a flow rate of about 500 µliters/minute. At this pressure, to achieve an average flow rate of 200 µliters/day (0.1389 µliters/min.), the ratio of time period T1 to time period T2 must be about $2.78 \times 10^{-4}$. A practical range for T1 is from 0.01 second to 2.0 seconds in duration. For T1 equal to 0.01 second, T2 should be about 35.99 seconds.

It is clear that for whatever configuration of tips 150, 160 and 170, including the number, size and orientation of slits, if any, it appears that a pressure exists that will cause an agent to flow virtually uniformly out of all the possible infusion outlet sites. Once this pressure has been found, a corresponding flow rate can be determined. Then, to calculate the ratio of T1 to T2 needed to produce a desired flow rate, the following equation is used:

Desired Average Flow Rate=T1(Flow rate during T1)/(T1+T2).

This equation can be rearranged to produce:

T1/T2=Desired Average Flow Rate/(Flow rate during T1–Desired Average Flow Rate).

For a given time for T1, T2 is found according to:

T2=T1/(Desired Average Flow Rate/(Flow rate during T1–Desired Average Flow Rate)).

Figure 17:
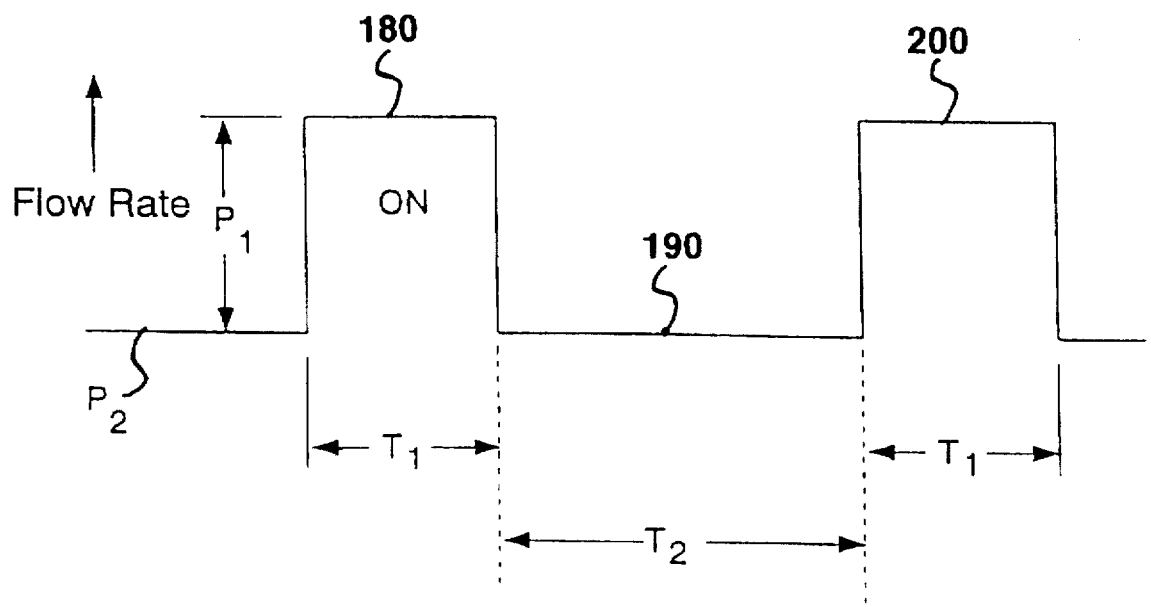
FIG. 17 is a timing diagram illustrating various pressure waves generated by the device on a liquid agent moved through the catheter.

The pressure waves shown in FIG. 17 may be achieved by any of the embodiments illustrated in the drawings. Referring to the embodiment in FIG. 7, the width of the pulse administered to motor 46 is varied to apply pressure wave 180 throughout time period T1. Thereafter, the motor is not pulsed again throughout time period T2 so that the pressure wave is reduced to level P2.

Referring to the embodiment shown in FIG. 9, valve 102 initially is closed and valve 101 initially is opened by pulses from module 32. At that time, arm 52 is rotated counter-clockwise as shown in FIG. 9 to draw fluid through valve 101 into section 140A of passageway 140. After fluid is drawn into section 140A, valve 101 is closed and valve 102 is opened by the application of suitable pulses from electronic module 32. Thereafter, the pulsing of motor 46 is reversed so that arm 152 rotates in a clockwise direction, thereby applying pressure wave 180 (FIG. 17) to the agent in catheter 22 and the tip of the catheter. Motor 46 thereafter is turned off in order to reduce the pressure to level P2 for time period T2 (FIG. 17).

Referring to FIG. 10, electronic module 32 is programmed to produce a pulse of current through solenoid coil 109 so that piston 105 is driven to the right as shown in FIG. 10. Before piston 105 is driven to the right, valve 101 is closed and valve 102 is opened, thereby applying pressure wave 180 to the fluid agent in catheter 22 and the catheter tip. At the end of the time period T1, electronic module 32 interrupts the flow of current through coil 109, opens valve 101 and closes valve 102. Piston 105 then returns to the position shown in FIG. 10 by the operation of spring 113, thereby drawing additional agent fluid through valve 101. The pressure in catheter 22 is reduced to pressure P2 by the closure of valve 102.

Referring to FIG. 11, prior to commencement of time period T1, valve 102 is opened and valve 101 is closed by the operation of electronic module 32. At the beginning of time period T1, motor 46 is stepped by a series of pulses so that worm gear 130 is turned in order to drive arm 134, connecting rod 107 and piston 105 to the right as shown in FIG. 11. Pressure P1 is thereby applied to the fluid agent in catheter 22 and the catheter tip through open valve 102.

At the end of time period T1, valve 102 is closed and valve 101 is opened. Thereafter, motor 46 is reversed in direction so that piston 105 returns to the position shown in FIG. 11, thereby drawing a new charge of fluid agent into cylinder 104.

Referring to FIG. 13, prior to time period T1, valve 102 is closed, thereby reducing the pressure in catheter 22 to pressure P2. Pressure is applied to the agent in passageway 140 by the operation of bellows 76 as previously explained. At the beginning of time period T1, valve 102 is opened by electronic module 32, thereby applying pressure P1 to the fluid agent in catheter 22 and the catheter tip. At the end of time period T1, valve 102 is closed, thereby reducing the pressure on the agent in catheter 22 to pressure P2 (FIG. 17).

The invention has been explained with reference to specific embodiments, configurations, flow rates and times. Those skilled in the art recognize that the disclosed embodiments, configurations, flow rates and times may be altered and modified without departing from a true spirit and scope of the invention as defined in the appended claims.

For example, valves 101 and 102 could have variable resistance to enable programmability, other types of pumps 44 could be used, and flow rates and times lower and higher than those specifically disclosed could be used as will be clear to those skilled in the art.

We claim:

1. A method for infusion of a predetermine dosage of liquid agent equally to a plurality of infusion sites located at spaced intervals in a portion of a body to be treated by said agent, said method comprising the steps of:

implanting, adjacent said portion of said body, a catheter defining a plurality of fluid exits responsive to a first pressure on said agent at or above a first threshold pressure, said first threshold pressure being the pressure that overcomes the outflow resistance of each and every said fluid exit and delivers substantially the same flow rate of said agent through each and every of said exits into said sites, said plurality of fluid exits responsive to a second pressure on said agent less than a second threshold pressure said second threshold pressure being the pressure wherein no agent flows from any of said exits into any of said sites;

applying to said agent a first pressure at or above said first threshold pressure during a predetermined first time period; and applying to said agent a second pressure at or below said second threshold pressure during a predetermined second time period, whereby said predetermined dosage is applied to each of said sites and the risk of underdosage and overdosage is reduced.

2. A method, as claimed in claim 1, wherein said fluid exits comprises a porous portion of said catheter.

3. A method, as claimed in claim 1, wherein said fluid exits comprise discrete ports.

4. A method, as claimed in claim 1, wherein said fluid exits comprise slits.

5. A method, as claimed in claim 1, wherein said first time period is substantially shorter than said second time period.

6. A method, as claimed in claim 1, and further comprising the step of adjusting said first and second pressures depending on the flow resistance of said fluid exits and the viscosity of said infusion sites.

7. A method, as claimed in claim 6, wherein said first and second pressures and said first and second time periods are adjustable to achieve an average flow rate of said agent through said catheter into all of said infusion sites in the range of 0.01 microliters per hour to 20 microliters per minute.

8. A method, as claimed in claim 1, wherein said second pressure is substantially zero.

9. A method, as claimed in claim 1, wherein said first time period is in the range from 0.01 second to 2.0 seconds.

10. A method, as claimed in claim 1, wherein said second time period is in the range from 8 seconds to 672 hours.

11. A method, as claimed in claim 1, wherein said flow rate through said catheter during said first time period is in the range from one microliter per minute to 5000 microliters per minute.

12. A method for infusion of a predetermine dosage of liquid agent equally to a plurality of infusion sites located at spaced intervals in a portion of a body to be treated by said agent, said method comprising the steps of:

implanting, adjacent said portion of said body, a catheter defining a plurality of fluid exits responsive to a first pressure on said agent at or above a first threshold pressure, said first threshold pressure being the pressure that overcomes the outflow resistance of each and every said fluid exit and delivers substantially the same flow rate of said agent through each and every of said exits into said sites, said plurality of fluid exits responsive to a second pressure on said agent less than a second threshold pressure, said second threshold pressure being the pressure wherein no agent flows from any of said exits into any of said sites;

applying a first pressure at or above said first threshold pressure to said agent within said catheter for a short time wherein the first pressure is sufficiently high to produce a substantially equal flow of said agent out of each of the said plurality of fluid exits and wherein the time the first pressure is applied is sufficiently short to produce the desired flow rate;

applying a second pressure at or below said second threshold pressure to said agent after said step of applying a first pressure wherein the second pressure is sufficiently low that no fluid exits any of said plurality of fluid exits.

13. A method, as claimed in claim 12, further comprising the step of priming said catheter with said agent.

14. A method, as claimed in claim 12, wherein said plurality of fluid exits comprises a porous portion of said catheter.

15. A method, as claimed in claim 12, wherein said plurality of fluid exits comprise discrete ports.

16. A method, as claimed in claim 12, wherein said plurality of fluid exits comprise slits.

17. A method, as claimed in claim 12, wherein said step of applying a second pressure at or below said second threshold pressure to said agent includes the step of applying a second pressure at or below said second threshold pressure to said agent for a time period that is substantially longer than said short time period that said first pressure is applied during said step of applying a first pressure at or above said first threshold pressure to said agent within said catheter.

18. A method, as claimed in claim 17, wherein said step of applying a second pressure at or below said second threshold pressure to said agent for a time period that is substantially longer than said short time period that said first pressure is applied includes the step of applying a second pressure at or below said second threshold pressure to said agent for a time period of from 8 seconds to 672 hours.

19. A method, as claimed in claim 12, and further comprising the step of adjusting said first and second pressures depending on the flow resistance of said fluid exits and the viscosity of said infusion sites.

20. A method, as claimed in claim 19, wherein said first and second pressures and said first and second time periods are adjustable to achieve an average flow rate of said agent through said catheter into all of said infusion sites in the range of 0.01 microliters per hour to 20 microliters per minute.

21. A method, as claimed in claim 12, wherein said second pressure is substantially zero.

22. A method, as claimed in claim 12, wherein said short time that said first pressure is applied in said step of applying a first pressure at or above said first threshold pressure to said agent within said catheter is in the range from 0.01 second to 2.0 seconds.

23. A method, as claimed in claim 12, wherein said flow rate through said catheter during said first time period is in the range from one microliter per minute to 5000 microliters per minute.

\* \* \* \* \*